United States Patent [19]

Poulsen

[11] Patent Number: 5,309,604
[45] Date of Patent: May 10, 1994

[54] COILING/UNCOILING DEVICE FOR TUBING

[75] Inventor: C. Eric Poulsen, Damascus, Md.

[73] Assignee: Merit Medical Systems, Inc., Salt Lake City, Utah

[21] Appl. No.: 29,789

[22] Filed: Mar. 11, 1993

[51] Int. Cl.$^5$ ............................................. A44B 21/00
[52] U.S. Cl. ........................ 24/16 R; 24/339; 24/543
[58] Field of Search .......... 24/16 R, 17 B, 18, 129 D, 24/335, 336, 339, 329, 543; 403/397

[56] References Cited

U.S. PATENT DOCUMENTS

| | | | |
|---|---|---|---|
| 1,716,628 | 6/1929 | Gittleman. | |
| 2,292,140 | 8/1942 | Lofgren | 24/129 D |
| 2,615,112 | 10/1952 | Lagan, Jr. | 219/19 |
| 2,696,963 | 12/1954 | Shepherd | 24/339 |
| 2,853,278 | 9/1958 | Hesler | 257/239 |
| 2,969,146 | 1/1961 | Metz | 206/65 |
| 4,002,349 | 1/1977 | Dopp | 24/339 |
| 4,116,338 | 9/1978 | Weichselbaum | 206/610 |
| 4,216,860 | 8/1980 | Heimann | 206/370 |
| 4,479,761 | 10/1984 | Bilstad et al. | 417/395 |
| 4,524,870 | 6/1985 | Roccaforte et al. | 206/608 |
| 4,707,892 | 11/1987 | Nelson | 24/336 |
| 4,850,954 | 7/1989 | Charvin | 604/4 |
| 4,900,184 | 2/1990 | Cleveland | 24/339 |
| 4,925,448 | 5/1990 | Bazaral | 604/171 |
| 5,027,478 | 7/1991 | Suhr | 24/16 R |
| 5,056,248 | 10/1991 | Blanchard | 24/543 |
| 5,163,554 | 11/1992 | Lampropoulos et al. | 206/363 |

FOREIGN PATENT DOCUMENTS

| | | |
|---|---|---|
| WO84/02893 | 8/1984 | European Pat. Off. . |
| 1152354 | 2/1958 | France . |
| 0467798 | 6/1937 | United Kingdom ........ 24/339 |

Primary Examiner—Victor N. Sakran
Attorney, Agent, or Firm—Workman, Nydegger & Jensen

[57] ABSTRACT

A clip device for holding flexible tubing in a coiled arrangement, where one end of the tubing is connected to an external device, such as an infusion pump. The clip has a bore formed through it at one end so that the clip may be slidably and permanently mounted on the flexible tubing. The clip also includes two C-shaped channels, one located at the bottom of the clip and the other along a side of the clip, that are sized to receive and frictionally engage the loops formed in the flexible tubing. The tubing is then coiled and firmly held in the coiled state by looping and engaging each loop in one of the C-shaped channels. The clip is capable of firmly holding the tubing in a coiled state, but the C-shaped channels are shaped and oriented on the clip such that when a user needs to use the flexible tubing, the user may pull on the free end of the flexible tubing whereby the loops are released from the C-shaped channels resulting in the uncoiling of the tubing. The tubing can also be quickly re-coiled and held by the clip in a coiled state again, ready for re-use.

2 Claims, 5 Drawing Sheets

COILING/UNCOILING DEVICE FOR TUBING

BACKGROUND

1. Field of the Invention

The present invention relates to a device which holds flexible tubing in a coiled state and yet permits quick uncoiling and recoiling of the tubing. More particularly, the present invention relates to a clip, permanently mounted to a piece of flexible medical tubing, which has channels for firmly holding the tubing in a tight and easy to access coil, yet wherein the channels are shaped and oriented such that a user pulls on one end of the tubing to quickly uncoil the tubing and use it for its intended purpose.

2. The Prior State of the Art

Flexible medical tubing is widely used in many procedures in modern hospitals, doctors, offices and the like. Although capable of being used for a variety of applications, medical tubing is frequently used to deliver intravenous fluids to a patient via a catheter. In this context, it is necessary for the tubing to remain completely sterile. At the same time, the tubing must be readily available to the medical technician for its intended purpose.

One example of such an application is arterial angiograph. This procedure involves injection of an x-ray sensitive dye into a catheter positioned in an artery to enable a clinician to observe accurately if obstructions are present in arteries, veins and ducts in various organs. A motor driven syringe, or infusion pump, is used to infuse the dye into the catheter.

Connected to the infusion pump is a portion of sterile flexible medical tubing. This piece of tubing is configured with a standard luer connector at each end. During initial set up procedures as shown by way of Example in the FIG. 1, one end of the sterile tubing 16 is connected to the infusion pump nozzle 14, and the opposite end 20 is left unconnected. However, it is imperative that the tubing remain sterile. Thus the tubing cannot simply hang from the infusion pump nozzle 14 because of the possibility it will come in contact with the infusion pump 12 or console 21, or some other non-sterile surface.

To prevent the tubing from coming in contact with a non-sterile surface, the prior practice has been to wrap the tubing 18 into a coil and to then tie-off the free end 20 by entwining it about a portion of the coil. This procedure has proven unsatisfactory for several reasons. First, the coil of tubing 18 often becomes unwrapped, either because it has not been tied of sufficiently or it is inadvertently knocked and uncoiled by a technician. As a result, the tubing may come in contact with a non-sterile surface and must be replaced. This wastes time and materials.

Another problem with the prior practice occurs when the technician must prime the pump with the injection dye. This is done by holding the bottle of dye with one hand and uncoiling the free end 20 of the tubing and placing it in the bottle with the other. This is often awkward and difficult to do, especially where the technician is rushing to complete the procedure.

Thus, the prior practice of tying off the end of the tubing to hold it in a manageable coil is often cumbersome and ineffective. The inability to quickly access the coiled tubing or a frequent need to replace a contaminated tubing adds both cost and time to the entire angiogram procedure.

BRIEF SUMMARY AND OBJECTS OF THE INVENTION

The present invention is directed to a coiling/uncoiling clip device for a length of flexible tubing. The device includes a novel clip that is fashioned such that it may firmly hold a piece of flexible tubing in an adjustable coiled state and yet still permit the tubing to be uncoiled by merely pulling on the free end of the tubing. The clip also allows the tubing to be re-coiled and held again in a coiled state ready for re-use.

In a preferred embodiment of the invention, the tubing is attached at one end, via a standard luer connector, to an infusion pump. The free end of the tubing is also fashioned with a standard luer connector, but is typically not initially affixed to any device.

The clip has at its top end a bore formed through it. This bore is dimensioned such that it may slidingly receive the tubing. This enables the clip to be permanently attached to the tubing prior to the tubing being fitted with the luer connectors. Although permanently attached, the bore is sized so as to permit the clip to slide and be positioned at any desired point along the length of the tubing.

The preferred embodiment of the clip further incorporates two C-shaped channels that are formed on it, one along the clip's side and one at the clip's bottom end. Each of these channels are sized such that they may receive and frictionally engage a portion of the tubing so as to form a loop in the tubing. In a preferred embodiment, the bottom C-channel may receive and engage two portions of the tubing in a side-by-side relationship, thus forming up to two loops, and the side C-channel may receive and engage another portion of the tubing, thus forming an additional loop. In this embodiment, the clip may thus hold a length of tubing in a coil of up to three loops, each loop being engaged and held at the C-channels. If only two coils are desired, then both loops of the coil may be attached at the bottom C-channel, or alternatively, one at the bottom C-channel and the other at the side C-channel. Similarly, if only one coil is desired, then the loop may be attached at the bottom C-channel or at the side C-channel.

Advantageously, the C-channels are sized such that they firmly hold the tubing in a coil until such time as the user desires to uncoil the tubing and use the tubing for its intended purpose. At that time, the user need only pull on the free end of the tubing and the tubing will disengage from each of the C-channels, thus causing the tubing to become uncoiled.

The position of the coiled tubing may be moved, relative to either end of the tubing, by sliding the clip along the length of the tubing prior to coiling. In this way, the coil may be moved closer to, or farther from, the infusion pump to which the tubing is connected.

The entire clip is constructed from a rigid, transparent material. Thus, the user is able to observe all portions of the tubing to ensure that there are not air bubbles present in the liquid within the tubing.

It is, therefore, a primary object of the present invention to provide a clip that is capable of permanently attaching to a flexible tubing and which is able to releasably hold the flexible tubing in a coiled relationship.

It is a further object of the present invention to provide a clip which permits for the quick uncoiling of the tubing by merely pulling on one end of the tubing.

It is yet a further object of the present invention to provide a clip which is positionable along the length of the flexible tubing whereby the position of the coils may be moved relative to the end of the tubing.

Still another object of the present invention is to provide a clip which permits for the tubing to be firmly held in a one, two, or three loop arrangement.

Another important object of the present invention is to provide a clip which may hold a tubing in a coiled relationship but that does not obstruct the view of the tubing so that the operator may ensure that the liquid within the tubing does not contain any bubbles.

Other objects and advantages of the present invention will become more fully apparent upon reading the following detailed description and appended claims, and upon reference to the accompanying drawings, or by practice of the invention.

Another important object of the present invention is to provide a clip which allows the tubing to be re-coiled and held by the clip in a coiled state, ready for re-use.

DETAILED DESCRIPTION OF THE PREFERRED EMBODIMENTS

Figure 1:
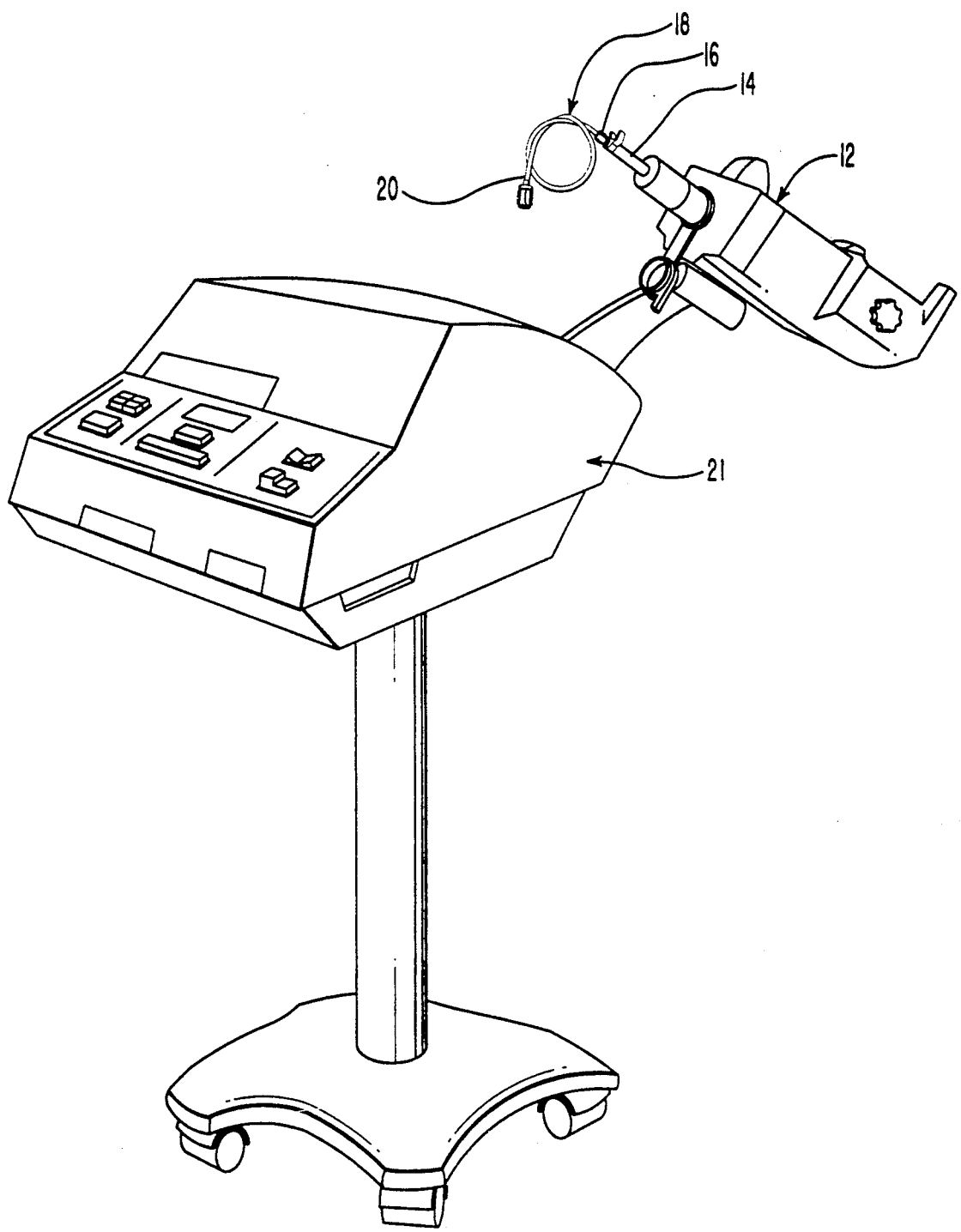
FIG. 1 is an illustration of the typical method used in the prior art for holding flexible tubing in a coiled relationship while it is attached to an infusion pump device.

Reference is now made to the drawings wherein like parts are designated with like numerals throughout. FIG. 1 illustrates the typical prior art practice as described above. The illustrated environment includes a standard infusion pump 12 which has an output nozzle 14. Connected to the nozzle 14 via a standard luer connector 16 is a sterile, flexible tubing 18. As is illustrated, the flexible tubing 18 is wrapped into a coil so as to keep the tubing 18 from hanging down or otherwise coming in contact with a non-sterile item such as console 21. As is further illustrated, the tubing 18 is held in the coiled position by tying off the free end 20 by entwining it around a portion of the coiled tubing 18. This is illustrative of the prior art practice with its attendant shortcomings, described above.

Figure 2:
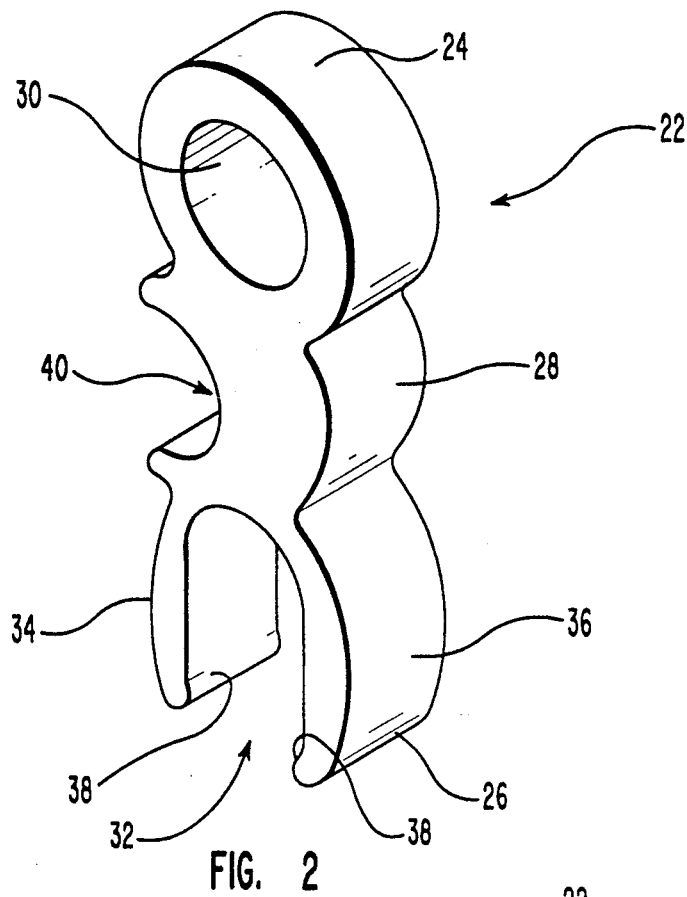
FIG. 2 is an enlarged perspective view of a presently preferred embodiment of the clip device of the present invention.

With reference now to FIG. 2, one presently preferred embodiment of the present invention is illustrated and designated generally at 22. The clip 22 has a body with a top end 24, a bottom end 26 and an intermediate portion 28. Located at the top end 24 is an attachment means, or a bore 30 formed through the clip 22. This bore 30 is dimensioned such that the clip 22 may be slidingly received along the length of the tubing 18, which is better illustrated in FIG. 3.

Figure 3:
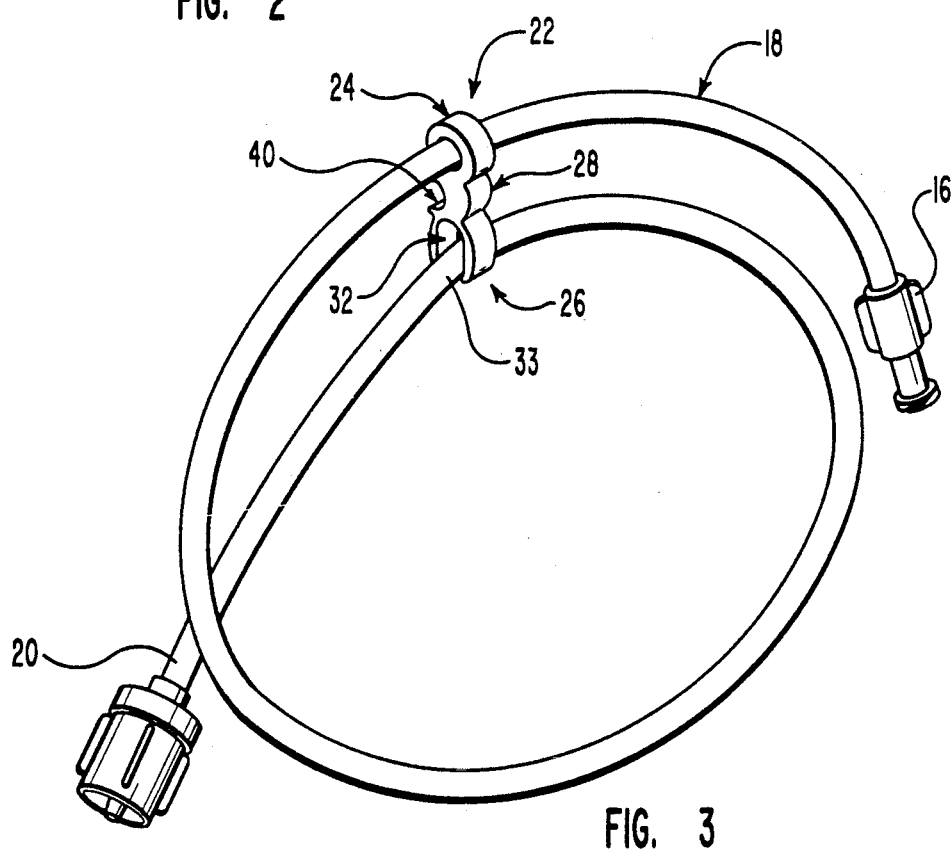
FIG. 3 is an illustration of the clip device of the present invention in operative association with a flexible tubing, where the clip device is used to hold the tubing in a single coil.

With continued reference to FIG. 2, the clip further includes a first means, or a first C-clip in the form of a C-shaped channel 32 that is formed at the bottom end 26 of the clip 22. This first C-shaped channel 32 is dimensioned such that it may receive and frictionally engage at least one concentric loop 33 (illustrated in FIGS. 3 and 4) formed by the flexible tubing 18. Preferably, the first C-shaped channel 32 is capable of frictionally engaging two loops in a side-by-side relationship, which is better illustrated in FIG. 4. Although capable of engaging two loops, the first C-shaped channel 32 may be used for frictionally engaging one loop, as is illustrated in FIG. 3. In an alternative embodiment, the first C-shaped channel 32 may be dimensioned so as to be capable of frictionally engaging only one loop.

Figure 6:
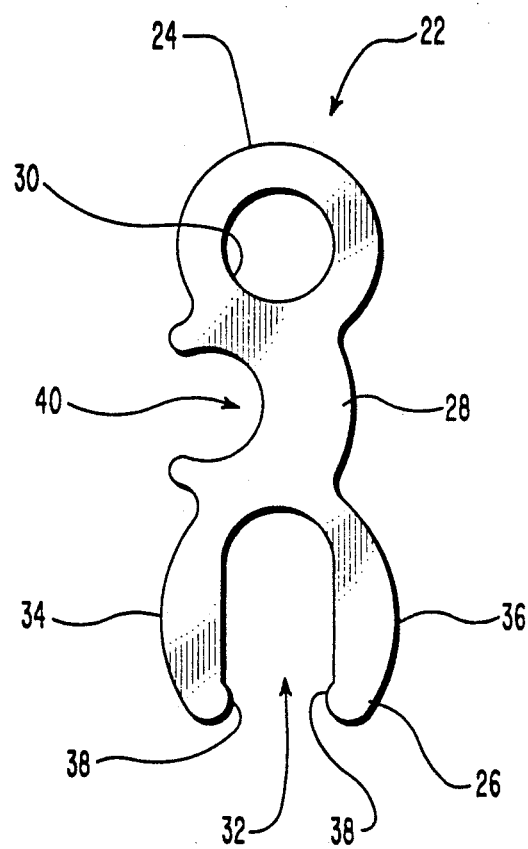
FIG. 6 is an enlarged side view of a presently preferred embodiment of the clip device of the present invention.

With reference now to FIG. 6, which illustrates a side view of the clip 22, the preferred configuration of the first C-shaped channel 32 is further shown. The C-shaped channel 32 has two downwardly extending, substantially parallel arms, a first-arm 34 and a second-arm 36. At the distal end of each arm, located at the bottom end 26 of the clip 22, the interiors of each arm 34, 36 form inwardly projecting and opposed lips 38. These opposing lips 38 on the arms 34, 36 serve to better engage and hold the flexible tubing 18, as is illustrated in FIGS. 3 and 4.

Again referring to FIG. 2, the clip 22 further includes a second means, or a second C-clip in the form of a C-shaped channel 40 that is formed in the intermediate portion 28 of the clip 22. This second C-shaped channel 40 is dimensioned such that it may receive and frictionally engage a concentric loop 33 that is formed in the flexible tubing 18. In the preferred embodiment, the second C-shaped channel 40 is capable of receiving and engaging only one loop as is illustrated in FIG. 4. As further shown in FIGS. 2 and 6, the openings to the channels 32 and 40 are orthogonal from one another to permit easier, unobstructed coiling and uncoiling of tubing 18.

Figure 4:
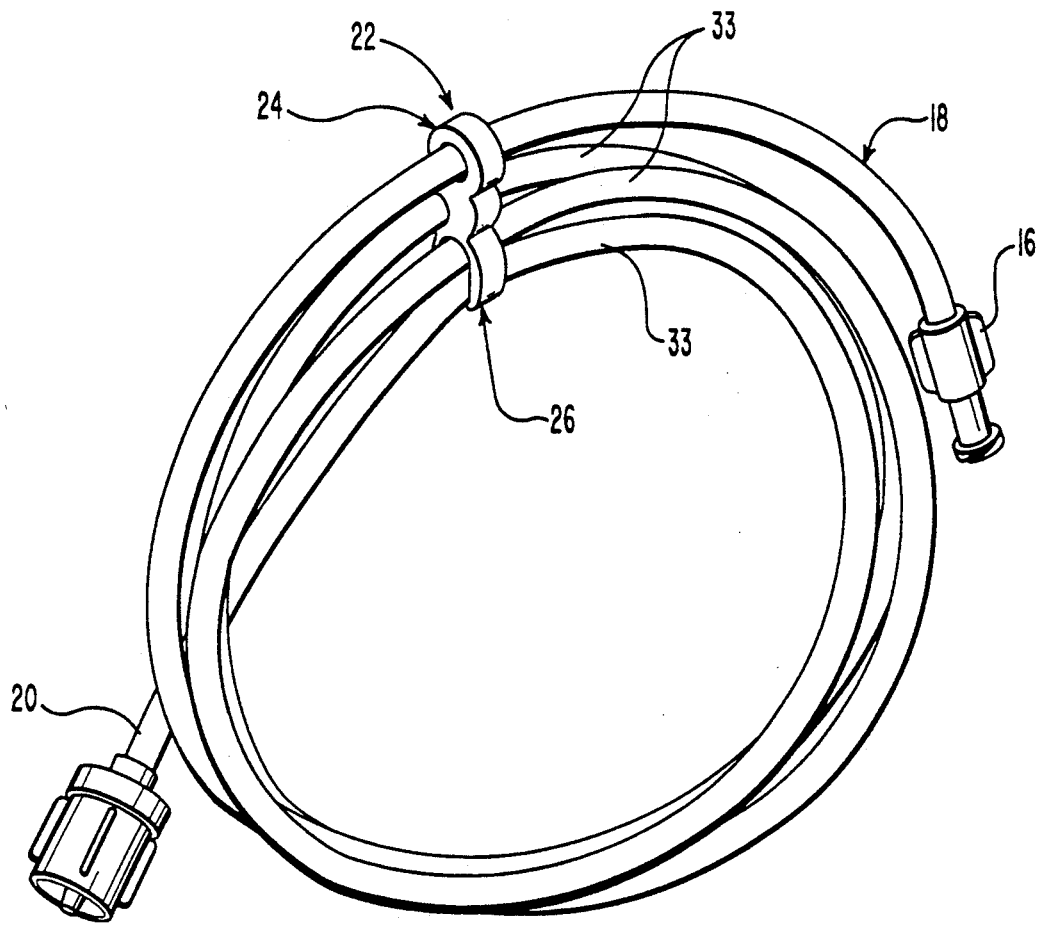
FIG. 4 is an illustration of the clip device of the present invention in operative association with a flexible tubing, where the clip device is used to hold the tubing in three coils.

As can be appreciated from FIGS. 3 and 4, in the presently preferred embodiment the user may wrap the flexible tubing 18 into a coil having one loop (as is illustrated in FIG. 3), two loops, or three loops (as is illustrated in FIG. 4). The first and/or second C-shaped channels 32, 40 hold the flexible tubing 18 in a substantially concentric coiled relationship, yet will quickly release the loops when a user pulls on the free end 20 of the flexible tubing 22, thus uncoiling the tubing 22.

Figure 5:
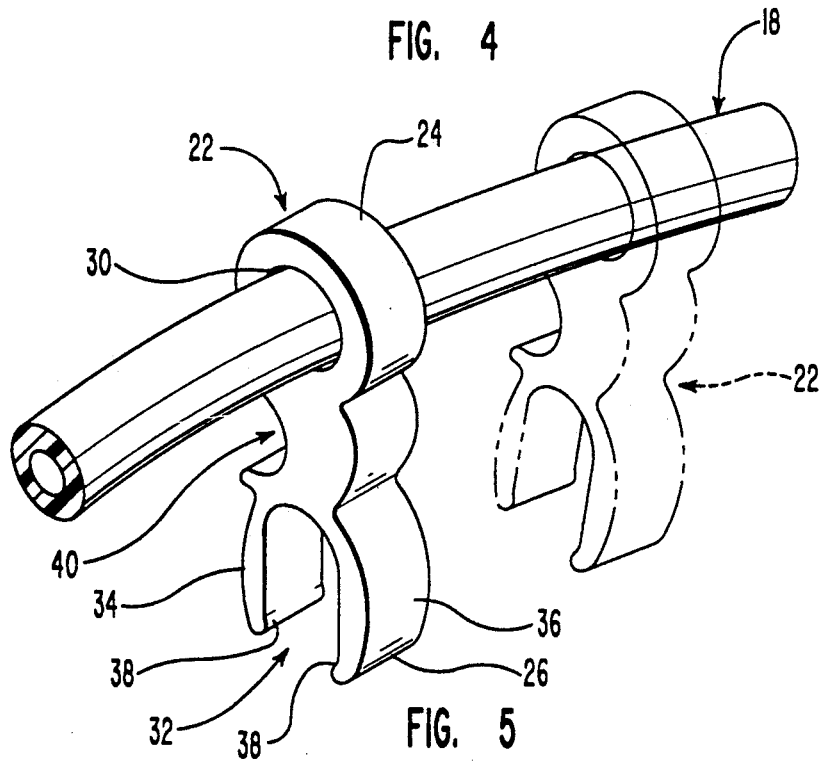
FIG. 5 illustrates the ability to slide the clip device of the present invention along the flexible tubing.
Figure 5A:
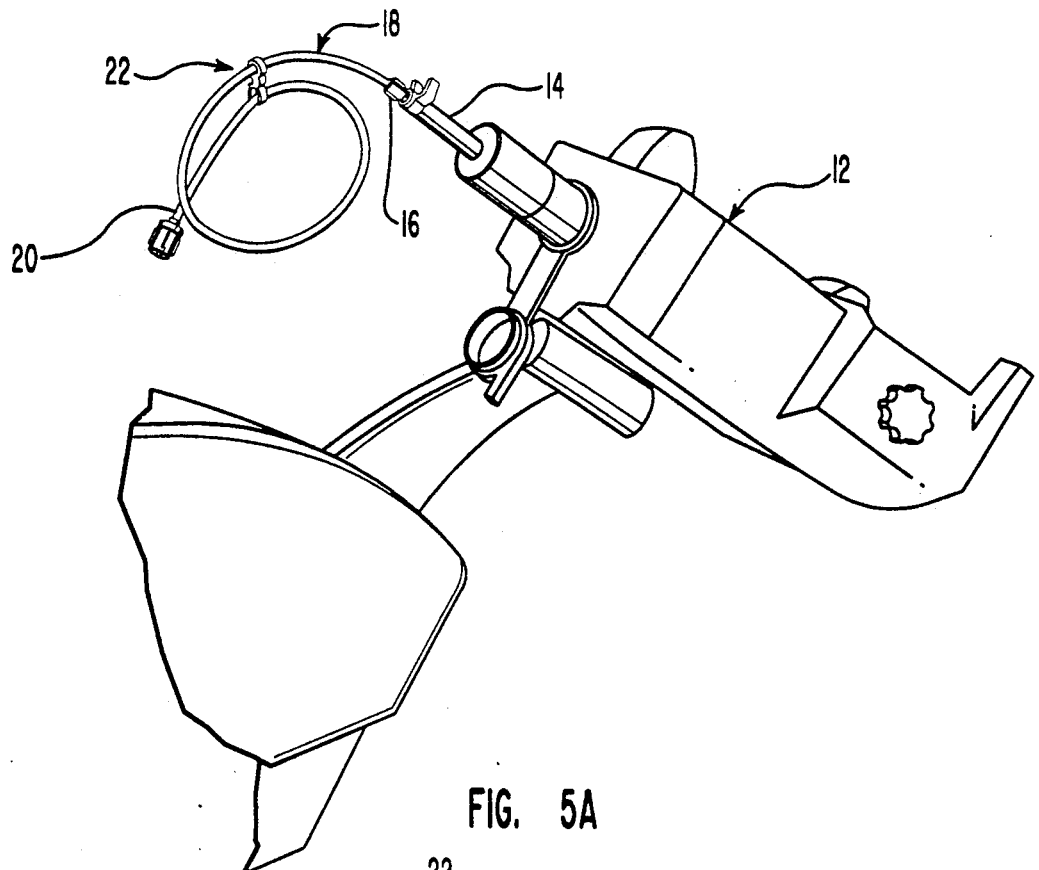
FIGS. 5A and 5B illustrate the significance of being able to slide the clip device of the present invention along the flexible tubing, illustrating how the coil may thus be selectively positioned relative to the infusion pump nozzle.
Figure 5B:
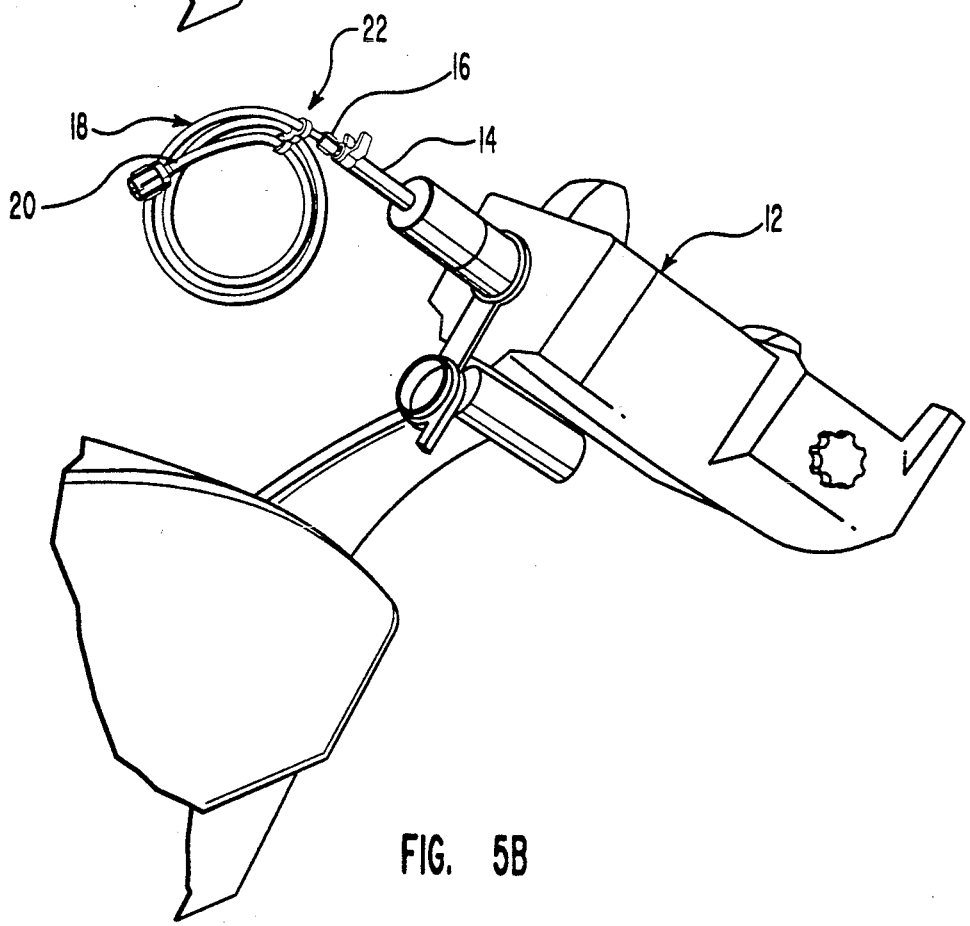

FIG. 5 illustrates the capability of the clip 22 to slide along the length of the tubing. FIGS. 5A and 5B are also illustrative of being able to slide the clip 22 along the length of the flexible tubing 18. By sliding the clip 22, the user may position the clip 22 to form a single coil, as in FIG. 5A, spaced farther from the nozzle 14, or may reposition clip 22 closer nozzle 14 to permit formation of more coils, held closer to the nozzle 14. Clip 22 can thus be easily adapted for various lengths to tubing 18, and to various preferences of the user. This capability also aids the user in positioning the coiled tubing 18 so as to avoid any contact by the flexible tubing 18 with a non-sterile object.

It will be appreciated by one skilled in the relevant art that a clip 22 according to the present invention may be made of a variety of materials. However, it is presently preferred that the clip 22 be made of a rigid but transparent material, such as a clear plastic. Thus, the clip will not obstruct the view of the contents of the flexible tubing 18 and the user can visually ascertain whether any air bubbles are present. Further, it is presently preferred that the clip 22 be permanently attached to the flexible tubing 18 prior to the time that the tubing is affixed with luer connectors at both ends.

It will be appreciated that the device of the present invention is capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A unitary one piece device releasably securing an elongate, flexible tubing that has a free end and an attached end joined to a support, the device securing the tubing in a plurality of substantially concentric loops that can be released by pulling downwardly on the free end, the device comprising:
   - a body have a top end, a bottom end, and an intermediate portion disposed between the top and bottom ends;
   - a closed circular member formed at the top end and completely encircling the flexible tubing so as to slidably mount the device to the flexible tubing between the free and attached ends thereof;
   - a first C-clip means formed at the bottom end and generally in line with the circular member and having a downwardly oriented opening that is large enough to receive and simultaneously hold more than one coil of the tubing for releasably securing at least two coils of the tubing in a friction fit; and
   - a second C-clip means formed at the intermediate portion and having an opening oriented toward a side and generally perpendicular to the first C-clip means for releasably receiving a third coil of the tubing in a friction fit, such that the coils of the tubing are released by each C-clip means by pulling down on the tubing near the free end thereof with one hand.

2. A device as defined in claim 1 wherein the material is transparent.

* * * * *

UNITED STATES PATENT AND TRADEMARK OFFICE
CERTIFICATE OF CORRECTION

PATENT NO. : 5,309,604
DATED : May 10, 1994
INVENTOR(S) : C. ERIK POULSEN

It is certified that error appears in the above-indentified patent and that said Letters Patent is hereby corrected as shown below:

Column 1, line 18, "doctors" should be —doctors—
Column 1, line 36, delete first occurrence of "the"
Column 1, line 50, "tied of" should be —tied off—
Column 6, line 3, "have" should be —having—

Signed and Sealed this

Twenty-ninth Day of November, 1994

Attest:

BRUCE LEHMAN

*Attesting Officer*     *Commissioner of Patents and Trademarks*